United States Patent [19]

Cheminal et al.

[11] Patent Number: 4,642,386
[45] Date of Patent: Feb. 10, 1987

[54] PROCESS FOR THE PREPARATION OF PURE HYDRATES OF FLUORAL AND OF HEXAFLUOROACETONE FROM HEMIACETALS

[75] Inventors: Bernard Cheminal, Lyons; Henri Mathais, Saint Didier au Mont d'Or; Marc Thomarat, Pierre-Benite, all of France

[73] Assignee: Atochem, France

[21] Appl. No.: 755,702

[22] Filed: Jul. 16, 1985

[30] Foreign Application Priority Data

Jul. 18, 1984 [FR] France .................. 84 11384

[51] Int. Cl.$^4$ .................. C07C 45/00
[52] U.S. Cl. .................. 568/405; 568/842; 568/486
[58] Field of Search .............. 568/599, 604, 842, 492, 568/411, 419, 495, 603, 604, 405, 486

[56] References Cited

U.S. PATENT DOCUMENTS

| | | | |
|---|---|---|---|
| 2,579,021 | 12/1951 | Brezesinska et al. | 568/599 |
| 2,616,929 | 11/1953 | Rosin | 568/492 |
| 2,848,500 | 8/1958 | Funck | 568/599 |
| 3,492,358 | 1/1970 | Hall | 568/492 |
| 4,467,124 | 8/1984 | Kawai et al. | 568/842 |

OTHER PUBLICATIONS

Guthrie, Can. J. Chem., vol. 53, pp. 898-906 (1975).
Middleton et al., J.A.C.S., vol. 86, pp. 4948-4952 (1964).

*Primary Examiner*—James H. Reamer
*Attorney, Agent, or Firm*—Brooks Haidt Haffner & Delahunty

[57] ABSTRACT

A process for preparing pure fluoral hydrate or hexafluoroacetone hydrate which comprises reacting a hemiacetal with the formula

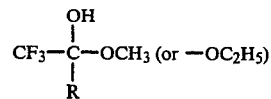

wherein R is hydrogen or $CF_3$, with water in a distillation column, removing respectively the methanol or ethanol produced at the head of the column, and recovering at the bottom of the column the pure hydrate so produced.

8 Claims, No Drawings

PROCESS FOR THE PREPARATION OF PURE HYDRATES OF FLUORAL AND OF HEXAFLUOROACETONE FROM HEMIACETALS

BACKGROUND OF THE INVENTION

The present invention relates to a process for preparing fluoral hydrate or hexafluoracetone hydrate, and more particularly, it relates to processes for the preparation of these hydrates in pure form from hemiacetals.

The fluoral and hexafluoroacetone hydrates are useful, particularly as intermediates for the synthesis of 2,2,2-trifluoroethanol and of 1,1,1,3,3,3-hexafluoroisopropanol, which are themselves useful starting materials for the synthesis of anaesthetics.

Fluoral hydrate is used herein to mean all of the following compounds described in the literature:

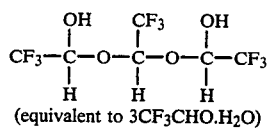
(equivalent to $3CF_3CHO.H_2O$)

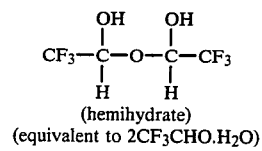
(hemihydrate)
(equivalent to $2CF_3CHO.H_2O$)

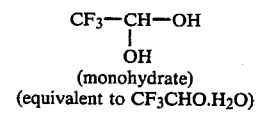
(monohydrate)
(equivalent to $CF_3CHO.H_2O$)

Hexafluoracetone hydrate has the structure of a gem-diol:

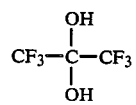

See W. J. Middleton and D. W. Wiley, 86 *J. A. C. S.* (1964) 4948, and C. G. Krespan and W. J. Middleton, *Fluorine Chemistry Reviews* 1(1), 145-196 (1967).

These hydrates containing trifluoromethyl radicals, as well as the hydrates containing chlorodifluoromethyl or dichlorofluoromethyl radicals which are present in the crude products, have melting points of the order of 50° to 60° C. and sublime at their melting points, which makes their separation by distillation impossible. See French Patent Application No. 2,493,836.

French Patent Application No. 2,493,836 describes a technique for purifying hexafluoroacetone containing chlorofluoroacetones. In essence, this consists of a chemical degradation, with the aid of basic compounds, such as calcium hydroxide, of the chlorinated by-products to produce compounds which can be separated by decantation after addition of an inorganic material, such as calcium chloride, which causes demixing of the liquid mixture. A pure hexafluoroacetone hydrate is then obtained. This process, which is not applicable to fluoral, requires a suitable treatment of the effluent water. In addition, this method is difficult to operate continuously. It is furthermore known from J. P. Guthrie, 53 *Can. J. Chem.* (1975) 898-906, that it is necessary to use a large quantity of water (a water/hemiacetal molar ratio greater than 50) to obtain an aldehyde hydrate from the corresponding hemiacetal.

THE INVENTION

The present invention accordingly provides a process which makes it possible to overcome these disadvantages and provides, continuously or batch-wise, a pure hydrate suitable for subsequent reaction, as for example, hydrogenolysis of fluoral hydrate to 2,2,2-trifluoroethanol.

The process according to this invention comprises reacting pure methyl or ethyl hemiacetal of the formula:

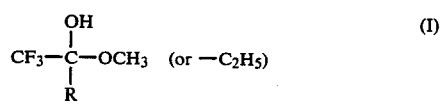

in which R is a hydrogen atom or the trifluoromethyl radical, with water in a distillation column with the concomitant respective formation of methanol or ethanol, distilling the methanol or ethanol at the top of the column, and recovering pure hydrate of fluoral (R is H) or of hexafluoroacetone (R is $CF_3$) at the bottom of the column. It will be understood that the hydrates so prepared do not contain chlorinated hydrates.

This process, which corresponds to the following reaction equation:

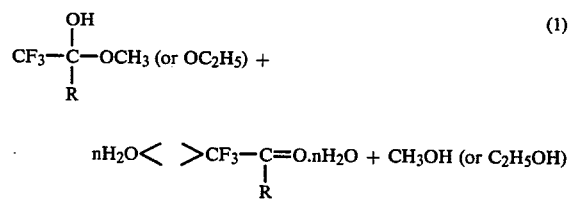

is described in further detail with respect to the methyl hemiacetal of fluoral, where R is hydrogen. It will be understood from the present disclosure that the process is readily applicable in the same manner and under the same conditions to the other hemiacetals of Formula (I).

The methyl hemiacetal employed in the process according to the invention is prepared in the crude state by absorbing the unrefined gases from the catalytic fluorination of chloral in pure methanol. These crude gases are freed from hydrofluoric acid beforehand and contain essentially fluoral ($CF_3CHO$), chlorinated by-products ($CF_2Cl$—CHO and $CFCl_2CHO$), light compounds such as $CHF_3$, $CCIF_3$, $CHF_2Cl$, $CHFCl_2$, CO), and hydrochloric acid. This absorption is preferably carried out at low temperature (approximately 0° C.) to avoid the secondary reaction:

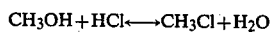

because the secondary formation of water leads to the production of various aldehyde hydrates whose very similar physical characteristics, namely, sublimation at their melting points and very similar boiling points, render it virtually impossible to separate them from the pure fluoral hydrate.

The crude methyl hemiacetal thus obtained, which can be neutralized with an aqueous solution of sodium carbonate, is then purified by conventional distillation at atmospheric pressure or under vacuum. It is preferred in certain embodiments of the invention to use a relatively short residence time, say, a few minutes, in the still pot of the distillation column used and, when there is no preliminary neutralization, to utilize an apparatus capable of withstanding corrosion by anhydrous hydrochloric acid gas.

Under these conditions, the amount of decomposition of the hemiacetal $CF_3$—$CH(OH)$—$OCH_3$ is low (below 1%), and the yield of pure product (boiling point: 97° C./750 torr) is excellent, namely, greater than 95%. If necessary, a methanol absorption tower may be provided in the vent circuit of the distillation column to recover the decomposed traces of fluoral. After decomposition in high vacuum at a high temperature, the heavy products (the chlorinated compounds) can be recycled to the preceding stage of chloral fluorination.

The hemiacetal, $CF_3$—$CH(OH)$—$OCH_3$, thus purified can be used as such in the present invention. It is reacted with water in a molar ratio $H_2O/CF_3$—$CH(OH)$—$OCH_3$ of from 1.5 to 3.0 at a temperature ranging from 95° to 115° C. and atmospheric pressure, in the pot of a distillation column, where the methanol formed during reaction (1) is removed at the top of the column as it is being formed. In certain preferred embodiments the water/hemiacetal ratio is approximately two and the temperature is from 100° to 110° C.

The distillation column can be one packed with rings, helices, woven packing, and the like, or it can be a plate column. When the operation is batch-wise, water and pure hemiacetal (water-soluble) are introduced simultaneously into the boiler and the reaction is carried to completion, that is, up until the time when the first hydrate vapor reaches the top of the column and when all distillation of methanol at the top ceases. For continuous operation of the process according to the invention, it is preferred to operate in a plate column to ensure, on each plate, the best possible contact between water (introduced on one of the plates above the boiler) and pure hemiacetal (introduced into the still pot or, preferably, between the pot and the plate on which water is introduced).

The methanol produced in the process according to the invention can be readily recycled to the preceding stage of absorption of crude gaseous fluoral, described above.

The process according to the invention more particularly provides a solution to the problem of separating 2,2,2-trifluoroethanol and methanol. These together form a maximum-boiling azeotrope, which causes a loss in yield of 2,2,2-trifluoroethanol. This is disadvantageous both to the profitability of commercial manufacture and to the purity of the recycled methanol.

All parts, percentages, proportions, and ratios herein are by weight unless otherwise stated.

The following Examples are given to illustrate embodiments of the invention as it is presently preferred to practice it. It will be understood that these Examples are illustrative, and the invention is not to be considered as restricted thereto except as indicated in the appended claims.

EXAMPLE I

Preparation of Pure Fluoral Hydrate

A distillation column 800 mm in height and having an inside diameter of 25 mm, filled with Multiknit metal plugs is employed. The still pot is heated with a thermostatted oil bath and the condenser is supplied with a cooling medium at a temperature of +3° to +5° C. This equipment operates at atmospheric pressure and a Timer automatic reflux divider regulates the proportion of liquid taken off at the top of the column.

The boiler is charged with 3.42 moles of water and 3.26 moles of pure hemiacetal, $CF_3$—$CH(OH)$—$OCH_3$, obtained as described above. Table I summarizes the operating conditions and shows the volume of methanol distilled.

TABLE I

| Time (hours and minutes) | Temperature °C. Top | Temperature °C. Bottom | Reflux Ratio | Volume of Methanol Distilled (in ml) | Notes |
|---|---|---|---|---|---|
| 0 h 15 | — | 92/93 | — | — | Start of boiling |
| 1 h 00 | 63.8 | 96 | — | — | |
| 1 h 30 | 63.9 | 98 | 9/1 | 10 | |
| 2 h 00 | 64.0 | 100 | " | 26 | |
| 2 h 30 | 63.9 | 102 | " | 44 | |
| 3 h 00 | 64.0 | 103 | " | 57 | |
| 3 h 30 | 87.0 | 104 | " | 71 | Reflux more difficult |

Then, 3.42 moles of water is added and the distillation at the top recommences (see Table II below). After this second addition of water, the molar ratio: water/hemiacetal is 2.1.

TABLE II

| Time (hours and minutes) | Temperature °C. Top | Temperature °C. Bottom | Reflux Ratio | Volume of Methanol Distilled (in ml) | Notes |
|---|---|---|---|---|---|
| 0 h 00 | — | — | — | — | Addition of water |
| 0 h 15 | 64.2 | 102 | — | — | Start of collection |
| 1 h 00 | 64.0 | 105.2 | 20/1 | 11 | |
| 1 h 30 | 64.0 | 107.0 | " | 19 | |
| 3 h 00 | 64.0 | 108.5 | " | 35 | |
| 4 h 45 | 64.0 | 109.2 | " | 35 | |
| 6 h 15 | 70.0 | 110.0 | " | 50 | End of the run |

The quantity of distilled methanol recovered relative to the theoretical quantity (104 g) present in the original hemiacetal is 93 percent. The hold-up in the column, which still contains methanol when the temperature at the top reaches and then exceeds 70° C., corresponds to the missing seven percent. Analysis of the methanol at the head shows the presence of 0.2 percent by weight of water (which can be readily removed with a molecular sieve). The organic impurities in the methanol (less than 0.01% by weight) do not interfere, and the methanol can accordingly be recycled to absorption of crude gaseous fluoral without any drawback. In case there is an inhibiting accumulation of these impurities, they can readily be separated from the methanol by a batch distillation.

The product collected at the bottom of the column is shown by NMR analysis to contain less than 0.1 percent by weight of methanol. Approximately 95 percent by weight of the product is the monohydrate, $CF_3$—$CH(OH)_2$, characterised by its $F^{19}$ fluorine and proton NMR analysis, and approximately five percent is the hemihydrate, $CF_3$—$CH(OH)$—$O$—$CH(OH)$—$CF_3$. The remaining water is associated with the monohydrate.

EXAMPLE II

Hydrogenolysis of Fluoral Hydrate

This Example illustrates the use of liquid fluoral hydrate prepared in Example I for the manufacture of 2,2,2-trifluoroethanol.

An autoclave with a working volume of approximately 100 ml and equipped with a magnetic bar stirrer is charged with 0.50 g of a catalyst containing five percent by weight of palladium deposited on active charcoal, sold by The Engelhard Corp., and 20.7 g (0.207 mole) of pure 2,2,2-trifluoroethanol. This mixture is heated for half an hour at 120° C. under a hydrogen pressure of 45 bars, and then 47.1 g of the product collected at the bottom of the column in Example I and 0.6 g of pure triethylamine co-catalyst are introduced gradually during 68 minutes, while the mixture is maintained at 120° C. and at 45 bars by successive additions of fresh hydrogen.

At the end of the fluoral hydrate introduction, the absorption of hydrogen lasts for about another five minutes and then ceases. The rate of reaction during introduction of the reactant represents 99 percent of the over-all reaction rate.

The autoclave is rapidly cooled and the catalyst is separated off by filtration outside the reactor, washed with water eight times and finally dried under vacuum, and is then recycled for two further identical runs, that is, using the same substrate and some catalyst charge.

Chromatographic analysis of the mixture produced indicates complete conversion of fluoral hydrate and a quantitative yield of 2,2,2-trifluoroethanol. This crude produce is readily purified by conventional means, such as distillation and, if necessary, final drying over a molecular sieve to separate any water.

The results obtained during these three consecutive runs using the same charge of catalyst are shown in Table III below.

TABLE III

| Run No. | Reaction Time (min.) | Conversion During the Introduction % | pH | Average Rate (Moles of CF$_3$CH$_2$—OH per g-at. Pd) |
|---|---|---|---|---|
| 1 | 73 | 99.0 | 9.95 | 983 |
| 2 | 52 | 98.5 | 9.85 | 1458 |
| 3 | 52 | 98.6 | 9.75 | 1484 |

The catalyst activity is not affected by the use of fluoral hydrate obtained by the process according to this invention. Such use has the advantage of requiring only a straightforward distillation of the aqueous solution of this alcohol to obtain very pure 2,2,2-trifluoroethanol. In this way the by-production of extremely toxic products, such as CFH$_2$—CH$_2$OH, which may accompany 2,2,2-trifluoroethanol, is obviated.

What is claimed is:

1. A process for the production of pure hydrates of polyfluoro materials, which process comprises reacting a hemiacetal having the formula:

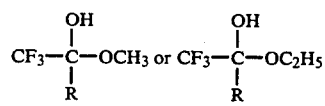

wherein R is hydrogen or trifluoromethyl, with water in a distillation zone to form, respectively, the corresponding fluoral hydrate or hexafluoroacetone hydrate and methanol or ethanol, removing the methanol or ethanol at the top of the distillation zone, and recovering the fluoral hydrate or hexafluoroacetone hydrate at the bottom of the distillation zone.

2. A process according to claim 1 wherein the molar ratio of water to hemiacetal is from 1.5 to 3.

3. A process according to claim 1 wherein the temperature is from 95° to 115° C. and the pressure is atmospheric.

4. A process according to claim 1 wherein the water and hemiacetal are introduced into the distillation zone together in a batch.

5. A process according to claim 1 wherein the operation is continuous and the hemiacetal is introduced into the distillation zone at a point below the point at which the water is introduced.

6. A process according to claim 1 wherein the hemiacetal is obtained by low temperature absorption in pure methanol or ethanol gases from the catalytic fluorination of chloral or hexachloroacetone, which gases have been cleansed of hydrofluoric acid and thereafter distilled.

7. A process according to claim 6 wherein the distillation of the chloral or hexafluoroacetone is carried out under a vacuum or at atmospheric pressure.

8. A process according to claim 6 wherein the methanol or ethanol from the distillation zone are used to absorb the fluorination gases.

* * * * *